United States Patent
Minocha et al.

(10) Patent No.: US 12,279,959 B2
(45) Date of Patent: Apr. 22, 2025

(54) METHOD OF MANUFACTURING MEDICAL IMPLANT

(71) Applicant: MERIL HEALTHCARE PVT. LTD., Gujarat (IN)

(72) Inventors: Pramod Kumar Minocha, Gujarat (IN); Deveshkumar Mahendralal Kothwala, Gujarat (IN); Arpit Pradipkumar Dave, Silvassa (IN)

(73) Assignee: Meril Healthcare Pvt. Ltd., Gujarat (IN)

( * ) Notice: Subject to any disclaimer, the term of this patent is extended or adjusted under 35 U.S.C. 154(b) by 480 days.

(21) Appl. No.: 17/789,220

(22) PCT Filed: Mar. 12, 2020

(86) PCT No.: PCT/IN2020/050227
§ 371 (c)(1),
(2) Date: Jun. 27, 2022

(87) PCT Pub. No.: WO2021/130764
PCT Pub. Date: Jul. 1, 2021

(65) Prior Publication Data
US 2022/0354653 A1     Nov. 10, 2022

(30) Foreign Application Priority Data
Dec. 27, 2019   (IN) .............................. 201921054123

(51) Int. Cl.
*A61F 2/30*      (2006.01)
*B22C 9/04*      (2006.01)
(Continued)

(52) U.S. Cl.
CPC .......... *A61F 2/30942* (2013.01); *B22C 9/043* (2013.01); *B33Y 80/00* (2014.12);
(Continued)

(58) Field of Classification Search
CPC ................................................. B21C 1/00–26
See application file for complete search history.

(56) References Cited

U.S. PATENT DOCUMENTS 3,894,572 A  *  7/1975  Moore, Jr. .............. B22C 1/165
                                                    427/403
5,118,727 A  *  6/1992  Roberts ............... C04B 35/6316
                                                    523/216
(Continued)

FOREIGN PATENT DOCUMENTS

CN       116748472 A  *  7/2023
IN      201921048709 A      12/2019

OTHER PUBLICATIONS

Walker et al., "3D Printing: Applications in evolution and ecology", Ecology and Evolution, vol. 9, Issue 7, Mar. 13, 2019, Lincoln, UK.

*Primary Examiner* — Jacob J Cigna
(74) *Attorney, Agent, or Firm* — Kunzler Bean & Adamson; Robert Gempeler (57) ABSTRACT

A method of manufacturing an implant is disclosed. The method includes preparing a wax template assembly based upon anatomical characteristics of an implantation site. Post formation of the template assembly, a lamination layer is provided over the template assembly resulting in a laminated template assembly. The lamination layer is composed of at least one polymer dissolved in one or more solvents. One or more coating layers of a pre-defined coating material are provided over the laminated template assembly to prepare a mold. The mold may then be sand-rained to form a sand coated mold. The sand coated mold may be de-waxed and baked for melting out the template assembly to form a de-waxed mold. A casting material is then poured over the de-waxed mold to form a casted mold which is cooled and solidified to form a casted implant which is further heat treated and finished to form the implant.

18 Claims, 7 Drawing Sheets

(51) Int. Cl.
*B33Y 80/00* (2015.01)
*C22F 1/10* (2006.01)
(52) U.S. Cl.
CPC ...... *C22F 1/10* (2013.01); *A61F 2002/30952* (2013.01); *A61F 2002/30957* (2013.01); *A61F 2002/30971* (2013.01); *A61F 2002/30985* (2013.01)

(56) References Cited

U.S. PATENT DOCUMENTS

| | | | | |
|---|---|---|---|---|
| 5,906,234 | A * | 5/1999 | Mastrorio | B22C 9/04 164/4.1 |
| 11,484,938 | B2 * | 11/2022 | Jing | B22C 25/00 |
| 12,097,553 | B2 * | 9/2024 | Dooley | B22C 1/183 |

* cited by examiner

METHOD OF MANUFACTURING MEDICAL IMPLANT

FIELD OF INVENTION

The present invention relates to medical implants, more specifically, the present invention relates to a method of preparing the medical implant.

BACKGROUND

Osteoarthritis and rheumatoid arthritis have become more common in the elderly population suffering from chronic joint disease and injuries caused by trauma. In order to address osteoarthritis and/or rheumatoid arthritis, total knee replacement surgery has proved to be an effective treatment in the current days. Knee replacement surgery involves removing an unhealthy portion of a femoral bone and tibial bone and replacing it with a metal prosthetic implant.

The conventional implants are fabricated using standard dimensions. The replacement of such conventional implants requires removal of diseased bone as well as unaffected bone (healthy bone) using various bone removal tools so that the standard sized implant can fit an implantation site. This intensive cutting process may lead to intense trauma and pain for a patient during the post-operational and recovery phases of surgery. In fact, it is documented that approximately 20% of total knee patients are not satisfied after the procedure because of their painful experiences which might last even for a long time. In addition, the post-operative treatments for attending to such pain are expensive and have least chances of optimal recovery. Moreover, there may be possibilities of dislocation of the knee implant segments as it might not fit with the bones perfectly.

Further, generally, the conventional implants are manufactured using metal 3D-printing technique. The implants manufactured through this technique have poor surface finish since the said process includes deposition of metal alloy layer by layer, (Ref: 3D Printing: Applications in evolution and ecology; Matthew Walker, Stuart Humphries; Ecology and Evolution. 2019; 9: 4289-4301.) The layer by layer deposition results in increased porosity as small cavities are formed within the part which leads to decrease in density of the 3D-printed implant. This affects the mechanical properties of the implants wherein decreased density makes the implants prone to cracks and damages under high loads and cyclic stresses.

Apart from the above procedure, methods involving wax template for fabrication of metal implants are also conventionally known. In such methods, one or more layers of coatings over a wax template are applied. Such coatings are approximately 4-6 mm thick so that the wax template can bear the molten metal at later stage. The application of multiple coatings over the fragile wax template results in development of micro-cracks and/or dots due to presence of viscous slurry coating with varying particle sizes having intensive and thick coating. Also, the wax template is often deformed by this procedure. As a result, such processes form implants having higher rejection rate. It is estimated that approximately 600 gms of precious medical grade metals like Co—Cr Alloys, Co—Cr—Mo Alloys, Titanium alloys etc. are wasted per every metal implant rejected. Thus, a higher rejection rate of conventional implants results in more wastage of metals (around thousands of kilograms of metal).

The resulting conventional metal implants as derived from the above disclosed processes, are vulnerable to deterioration caused by scratching, wear or damage through the corrosive processes that occur in situ once installed. Damaged implants may exhibit diminished performance, and in some cases, must be repaired or replaced. Implants including metallic substrates having materials such as steel, cobalt, titanium, and alloys thereof, are also vulnerable to damage or mechanically-assisted corrosion that can lead to loss of structural integrity, scratching or increased wear rates and reduction of implant performance. Traditional approaches for improving the scratch and wear-resistance of metallic orthopaedic implants include surface treatments such as ion implantation, gas nitriding, high temperature oxidation, coating techniques, etc.

However, certain limitations such as inability, poor adherence of coatings to underlying substrates, and/or economic feasibility may abridge the utility of some of these methods.

SUMMARY

The present invention discloses a method of manufacturing an implant. The method includes a set of pre-defined steps. The method includes preparing a template assembly based upon one or more anatomical characteristics of an implantation site. The template assembly is made from wax. Followed by formation of the template assembly, a lamination layer is provided over the outer surface of the template assembly resulting in a laminated template assembly. The lamination layer is composed of at least one polymer dissolved in one or more solvents. Subsequent to the aforesaid, one or more coating layers of a pre-defined coating, material are provided over the laminated template assembly to preparing a mold. The mold may then be sand-rained to form a sand coated mold. The sand coated mold may be de-waxed and baked for melting out the template assembly to form a de-waxed mold. A pre-defined casting material is then poured over the de-waxed mold to form a casted mold which is subsequently cooled and solidified to form the casted implant. The casted implant may be further heat treated and finished to form the implant.

The foregoing features and other features as well as the advantages of the invention will become more apparent from the following detailed description, which proceeds with reference to the accompanying figures.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein. Moreover, those in the art will understand that the drawings are not to scale.

DETAILED DESCRIPTION OF THE DRAWINGS

Prior to describing the invention in detail, definitions of certain words or phrases used throughout this patent document will be defined: the terms "include" and "comprise", as well as derivatives thereof, mean inclusion without limitation; the term "or" is inclusive, meaning and/or; the phrases "coupled with" and "associated therewith", as well as derivatives thereof, may mean to include, be included within, interconnect with, contain, be contained within, connect to or with, couple to or with, be communicable with, cooperate with, interleave, juxtapose, be proximate to, be bound to or with, have a property of, or the like; Definitions of certain words and phrases are provided throughout this patent document, and those of ordinary skill in the art will understand that such definitions apply in many, if not most, instances to prior as well as future uses of such defined words and phrases.

Particular embodiments of the present disclosure are described herein below with reference to the accompanying drawings, however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The term "implant" refers to a substitute for the damaged bone, tissue etc., which is fabricated artificially to match the damaged portion of the bone, and which is attached to a patient undergoing knee replacement surgery.

The term "implantation site" refers to a treatment location where the implant is deployed. Though the implantation site in the present invention may be any treatment location of a patient, however, as an exemplary embodiment of the following description, the implantation site corresponds to native bones of a knee.

In accordance with the present disclosure, a method for fabrication of a medical implant (or implant) is disclosed. In an embodiment, the method of the present invention results in the formation of a knee implant made of a metal alloy.

The method of the present invention involves reduced cost and simpler machinery as compared to the conventional methods. The method of the present invention involves a simple 3D-printing mechanism using wax patterns as opposed to the sophisticated metal alloy 3D-printers used in conventional methods. Hence, the present method provides minimum exposure of metal alloy to higher temperatures which helps to retain the tensile strength of metals and other desired metallic properties.

The method of the present invention involves various steps such as precision metal casting, finishing, machining, surface treating, etc. The aforesaid steps are followed in a sequential manner to obtain the implant which may either have a standard size or may include a customized size based upon one or more anatomical characteristics of an implantation site.

Such customization in the present invention eliminates the risks of inadequate fixation of the implant at the implantation site thereby proving an optimal fit as well as functionality of the implant at the implantation site.

The process includes preparing a wax template assembly and then laminating the same followed by coating the assembly in ceramic slurry and subsequently pouring a metallic solution to cast an implant. The step of providing a lamination layer over the template assembly helps the template assembly to withstand stress and/or forces encountered during subsequent steps of the present process so that the shape of the template assembly remains intact. Also, the lamination layer eliminates the chances of dot impression and micro-cracks formation which may develop during subsequent steps of the present process thereby reducing the rejection level of the implants to about 10%.

Manufacturing the implants using the method of the present invention, results in implants with smooth surface and optimum density that is required for preventing cracks on when subjected to cyclic stress and loads.

Figure 1:
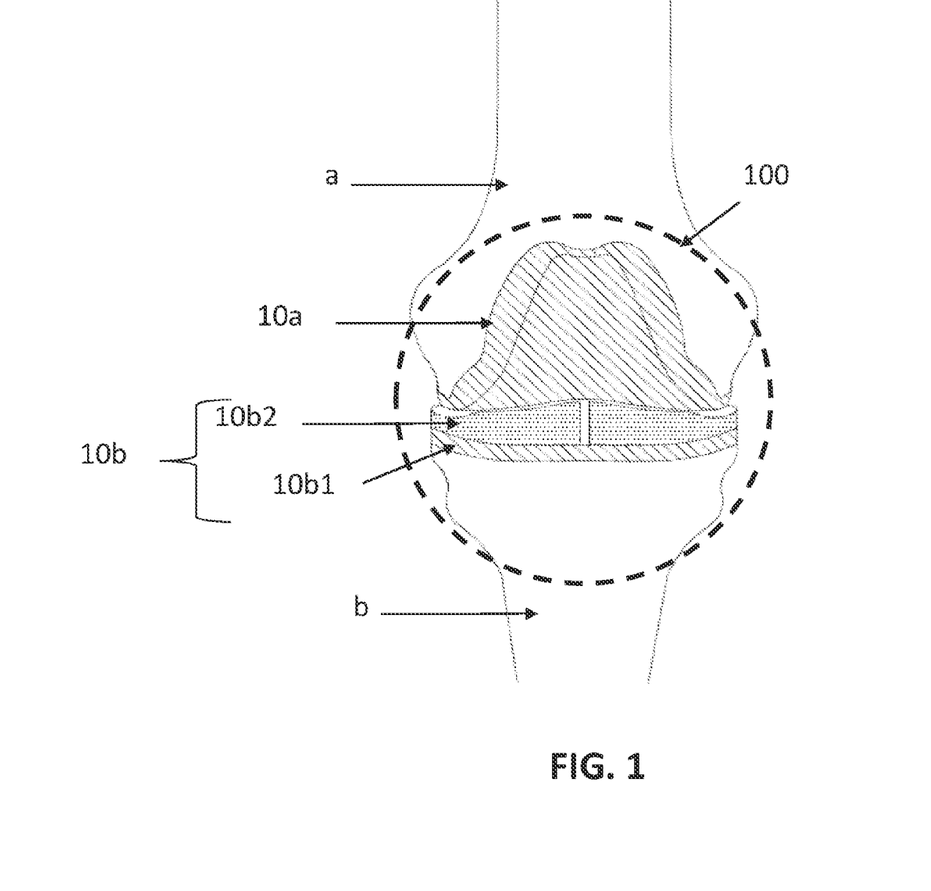
FIG. 1 represents an implant 100 deployed at an implantation site in accordance with an embodiment of the present invention.

Now specifically referring to figures, FIG. 1 depicts the implant 100 when implanted at the implantation site. As evident from the said figure, the implant 100 is a knee implant. However, the implant 100 may be any other implant such as, without limitation, a hip, an ankle joint, a shoulder joint, an elbow, a spine, etc.

The implant 100 may be made from a material that provides adequate strength and rigidity at the implantation site. The materials may include without limitation metals, metal alloys, ceramic materials, biocompatible materials, etc. The examples of the materials include, without limitation, commercially pure Ti (cpTi), medical grade stainless steels, tantalum, cobalt chromium molybdenum alloy (CoCrMo), cobalt chromium alloy (CoCr), titanium alloys, tantalum alloys, Nitinol, Ti—Al—V (titanium-Aluminum-vanadium), etc. In an embodiment, the implant 100 of the present invention is made from cobalt chromium molybdenum alloy (CoCrMo).

The implant 100 as depicted in FIG. 1 includes three basic components namely a femoral component 10*a*, a tibial component 10*b* and a patella component (not shown). The femoral component 10*a* fits at a lower end of a native femoral bone 'a'. The tibial component 10*b* fits at an upper end of a native tibial bone 'b'. The tibial component 10*b* further includes a tibial base plate 10*b*1 and a tibial insert 10*b*2. The tibial insert 10*b*2 is disposed between femoral component 10*a* and tibial base plate 10*b*1. The patella component fits on a back side of a native kneecap.

The femoral component 10*a* and the tibial base plate 10*b*1 may be made of any metal material such as surgical grade stainless steel (SS 316L), cobalt chromium alloys, pure commercial titanium (Ti) and/or titanium alloys. In an exemplary embodiment of the present invention, cobalt chromium molybdenum (CoCrMo) alloy material is used for manufacturing the femoral component 10*a* and the tibial base plate 10*b*1.

The tibial insert 10*b*2 can be made from a plurality of materials not limited to Ultra highly cross linked polyethylene (UHXLPE), UHMWPE, methyl methycrylate, PEEK (Polyether ether ketone), Polycarbonate (PC), etc. In an exemplary embodiment of the present invention, the tibial insert 10*b*2 is made of UHMWPE (Ultra-high-molecular-weight polyethylene) material. The patella component (not shown) is made of one or more materials UHXLPE, UHMWPE, PEEK, etc. In an embodiment of the present invention, the patella component (not shown) is made from UHMWPE.

Further, the implant 100 may be made from a pre-defined method as defined in FIG. 2 below. In an embodiment, the implant 100 formed from the said method is fabricated and dimensioned as per the anatomical characteristics of the implantation site resulting in a customized implant having maximized conformability with the anatomy of the implantation site. It is important that the implant 100 mimics the anatomy and physiology of the natural knee joint as the same provides maximum conformability and restores the function of a damaged knee properly. The accurate dimensions of the implant 100 promote magnificent flexion, thereby improving the patient's comfort.

Alternately; the implant 100 may be made of standard dimensions.

Figure 2:
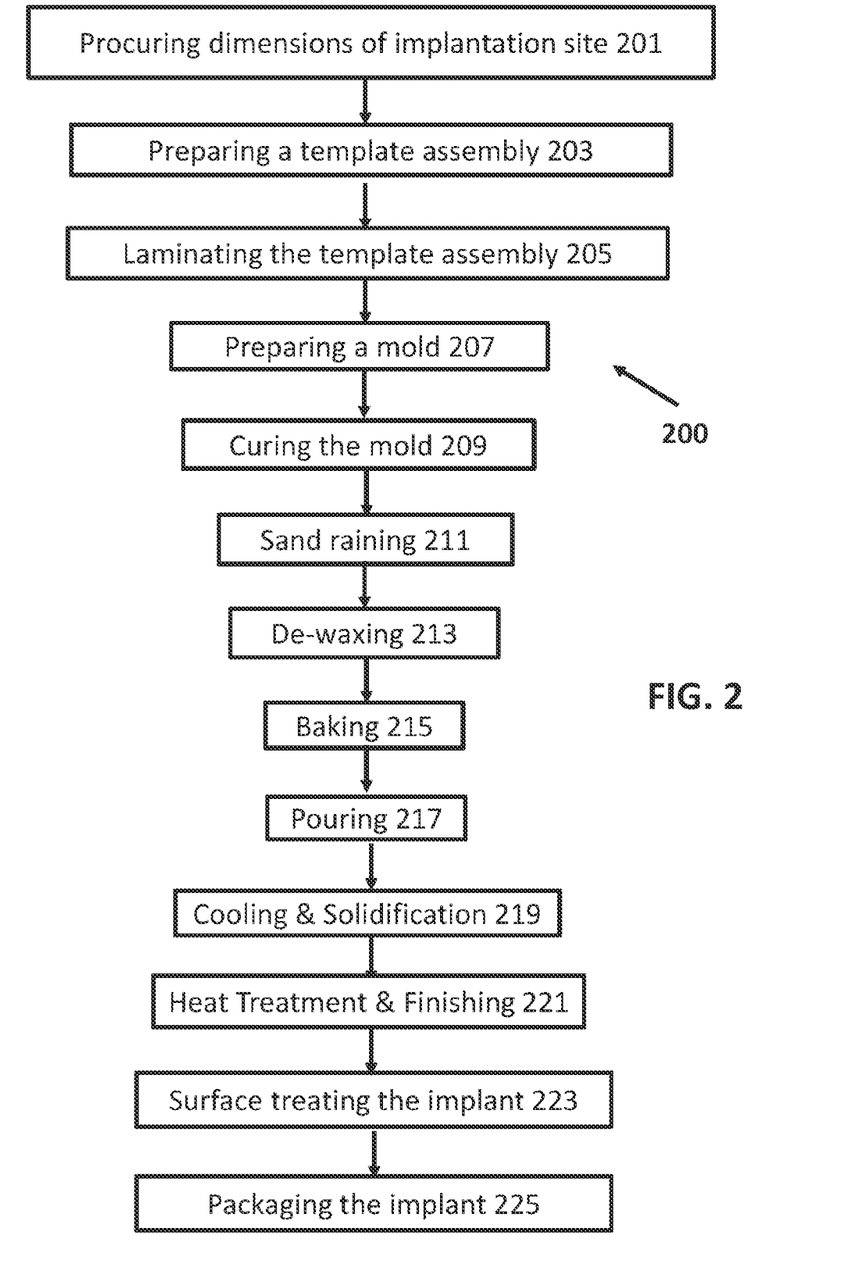
FIG. 2 depicts a flow chart depicting the method of implant preparation in accordance with an embodiment of the present invention.

FIG. 2 of the present invention illustrates a flow chart depicting the method of manufacturing the implant 100. The process commences at step 201 in which the anatomical characteristics (e.g., thickness, curvature and/or size) of the implantation site as well as an area surrounding the implantation site are procured. The said characteristics of the implantation site may be obtained using a conventional imaging technique such as, without limitation, ultrasound, MRI (Magnetic Resonance Imaging), CT scan (computerized tomography scan), X-ray imaging, fluoroscopic imaging, etc. Obtaining said characteristics helps in manufacturing the customized implant 100, namely, an implant with dimensions customized to a patient's anatomical characteristics.

The customized implant 100 provides maximum conformability and avoids inadequate fixation of the implant 100 thereby minimizing the bone cutting process. Further, the duration for performing surgery is significantly reduced as cutting of healthy bones is minimized. The customized implant 100 overcomes the rotation problem of the conventional implants which leads to persistent pain post knee replacement surgery.

At step 203, the anatomical characteristics obtained at step 201 are used to develop a template assembly 20 (or a customized template assembly 20) having an outer surface. Optionally/alternately, the step 201 may be omitted and the template assembly 20 may be formed using standard dimensions.

In an embodiment, the template assembly 20 is a wax assembly. Wax is used to form the template assembly 20 due to its superior properties such as, low melting point, easy molding and economical availability, ease in recycling, toxicity, resistance to binders, etc. The wax used in the present invention may include, without limitation, paraffin wax, bees wax, montan wax, carnabua wax, blend of wax, etc.

Figure 3A:
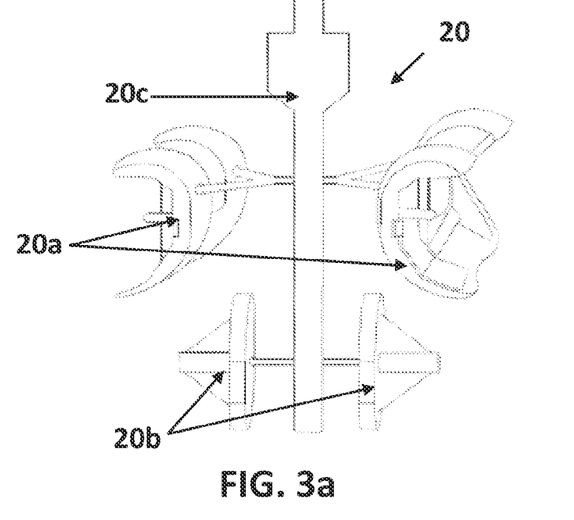
FIGS. 3(a)-3(k) depicts the different stages of FIG. 2 in accordance with an embodiment of the present invention.

The template assembly 20 may be a single structure. Alternately, multiple components may be joined with each other to form the template assembly 20. In an embodiment, the template assembly 20 is made from multiple components like a master wax cavity, wax components, etc. The master wax cavity may be a central part to which the wax components are attached. FIG. 3*a* illustrates the template assembly 20 with femoral and tibial components 20*a*, 20*b* (wax components) attached to a master wax cavity 20*c*.

The template assembly 20 may be developed using an additive manufacturing process based upon the anatomical characteristics of the implantation site. In an embodiment, the process of developing the template assembly 20 is fused deposition modeling (FDM). As an exemplary process, the template assembly 20 is created directly from a digital three-dimensional model, say a 3D computer-aided design model, using a layer-by-layer deposition of a feedstock material, say, wax, extruded through a nozzle.

In an embodiment, the FDM process starts with importing a .STL file of the model into pre-processing software. This model is oriented and mathematically sliced into horizontal layers of pre-defined thickness. The said sliced model is then used to create the template assembly 20 layer by layer.

The template assembly 20 is maintained at a temperature not more than 25° C. In an embodiment, the template assembly 20 is maintained between 22° C. to 24° C.

Figure 3B:
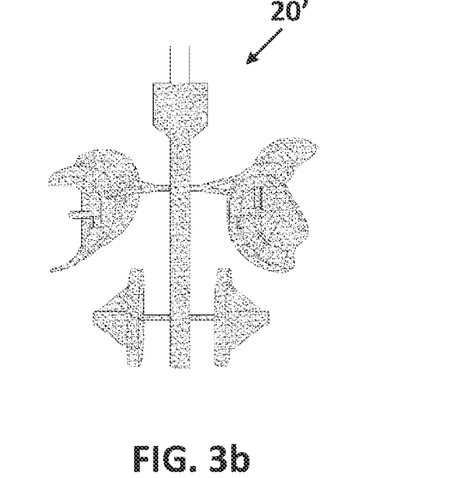

At step 205, the template assembly 20 as prepared in step 203 is further laminated to form a laminated template assembly 20' (as shown in FIG. 3*b*). Lamination of the template assembly 20 helps the template assembly 20 to withstand stress and/or forces encountered during subsequent steps of the present process so that the shape of the template assembly 20 remains intact. Also, lamination over the outer surface of the template assembly 20 eliminates the chances of dot impression and micro-cracks formation which may arise during subsequent steps of the present process thereby reducing the rejection level of the implants to about 10%.

Further, lamination helps in complete removal of wax during autoclaving and minimizes residual wax inside a mold during de-waxing procedure (described below).

The selection of material used for lamination is critical. The material(s) used for lamination should be compatible with the template assembly 20, should bond well with the template assembly 20, should not be tacky and should be easily removable without harming the template assembly 20. Further, the material(s) for lamination should be compatible with the mold (described below).

The lamination may be provided by applying one or more lamination layers 'IL'. In an embodiment, one lamination layer 'LL' is provided.

Figure 4:
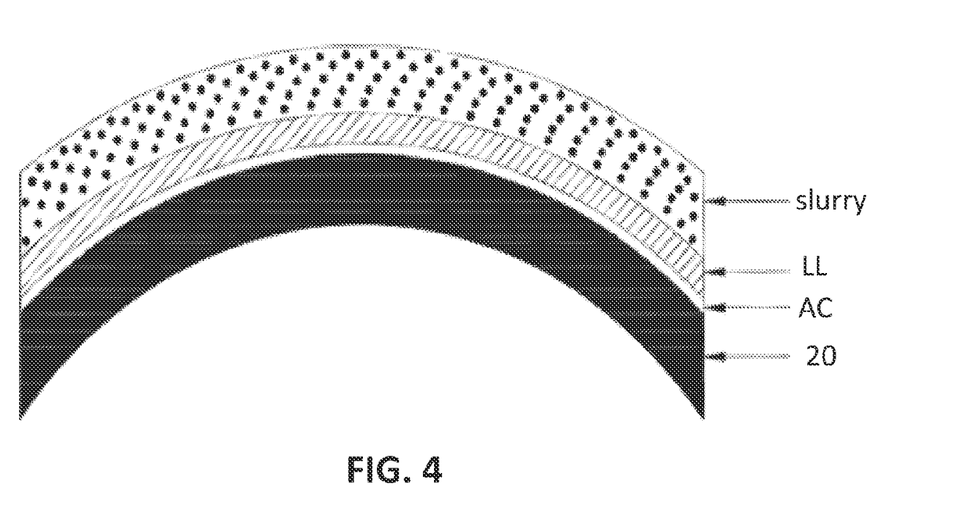
FIG. 4 depicts the layers provided on the template assembly 20 in accordance with an embodiment of the present invention.

In an embodiment, prior to applying the lamination layer 'LL', an adhesive coat 'AC' may be provided over the template assembly 20 as shown in FIG. 4. In an embodiment, the adhesive coat 'AC' is applied by coating a resin solution having one or more resins dissolved in at least one solvent.

The resins which may be used in the present invention include without limitation polyvinyl acetate resins, hydrocarbon resins, phenol—formaldehyde resins, polyamide resins, polyester resins ketonic resins, poly urethane resins, epoxy resins etc. or their derivatives and/or combinations thereof. The concentration of the resins may range between 10 wt % to 30 wt %, more preferably, ranges between 10 wt % to 20 wt %. In an embodiment, the concentration of the resins is 15 wt %.

The solvents may include acetone, isopropyl alcohol, chloroform, tetrahydrofuran, methyl chloride, toluene, acetonitrile, methylene dichloride (MDC), ethylene dichloride (EDC), trichloro ethane, etc. or combinations thereof. The concentration of the solvents may range between 60 wt % and 90 wt %.

In an embodiment, the adhesive coat 'AC' includes polyamide resin as resin in a concentration of 15 wt % and iso propyl alcohol (IPA) as solvent in a concentration of 85 wt %.

The adhesive coat 'AC' may be applied using techniques such as dip coating, brush coating, spray coating, etc. In an embodiment, brush coating is used to apply the adhesive coat 'AC' over the template assembly 20. The adhesive coat 'AC' may be applied as a single layer or multiple layers. The thickness of the adhesive coat 'AC' may range between 2 μm and 6 μm. In an embodiment, the thickness of the adhesive coat 'AC' is 4 μm.

The adhesive coat 'AC' promotes better adhesion between the template assembly 20 and the lamination layer 'LL'.

The lamination layer 'LL' is a protective layer which may be coated over the adhesive coat 'AC' as shown in FIG. 4. In an embodiment, the protective layer is provided by coating a polymeric formulation over the adhesive coat 'AC'. The polymeric formulation may be prepared by dissolving at least one polymer in a solvent or a mixture of solvents.

The polymers with a high melting point may be used in the present invention. Such polymers may include, but not limited to, polypropylene, polyethylene (high density polyethylene and/or low density polyethylene), polyvinyl pyrrolidone (PVP), PLA, PGA, PDLA, Poly L-lactide co-caprolactone (PLCL) or combinations thereof. In an embodiment, LDPE is used in the protective layer.

The melting temperature of LOPE ranges from 100° C. to 135° C., more preferably between 105° C. to 120° C. The molecular weight ranges from 1,000 g/mol to 70,000 g/mol and more preferably ranges from 10,000 g/mol to 40,000 g/mol. The concentration in of the polymer may range from 5 wt % to 40 wt % and more preferably ranges from 10 wt % to 25 wt %.

The solvents used in the present invention may include, without limitation, acetonitrile, methylene dichloride (MDC), ethylene dichloride (EDC), trichloro ethane, benzene, acetone, ethanol, isopropyl alcohol, DMF, tetrahydrofuran (THF), hexafluoro Isopropanol, dimethyl sulfoxide (DMSO), or combinations thereof. The concentration of the solvents may range between 50 wt % to 90 wt %.

In an embodiment, the polymeric formulation includes low density polyethylene as polymer and trichloro ethane as solvent in the concentration of 15 wt % and 85 wt % respectively.

The coating can be applied either by dip coating, spray coating, brush coating, spin coating, etc. In an embodiment, the lamination layer 'LL' is achieved by spray coating technique. The spray coating parameters are very critical. Such parameters mainly include inert gas pressure, distance between spray gun and template assembly, solution flow rate, rotation per minute, etc.

In an embodiment, the distance between the spray gun and the template assembly 20 may range from 20 mm to 100 mm and more preferably from 40 mm to 70 mm. The rotation per minute may range from 15 rpm to 50 rpm with a solution flow rate ranges from 0.10 ml per minute to 5.0 ml per minute. The nitrogen pressure may range from 10 psi to 35 psi which helps in uniform deposition of particles to form a lamination layer 'LL'.

The coating thickness of the protective layer may range between 10 μm and 80 μm and more preferably between 30 μm and 50 μm.

At step 207, a mold 30 is prepared, The said mold 30 may be made from a material including, without limitation, plaster of paris, ceramics, clay etc. In an embodiment, a ceramic material is used for the preparation of mold 30 owing to its thermal resistant property.

As a pre-requisite to preparation of the mold 30, ceramic slurry is prepared. In the present invention, the ceramic slurry is a mixture of liquid refractory binders and refractory powders. The ceramic slurry may include colloidal silica, silica sand, alumino-silicates, alumina, fused silica, zirconium silicate, etc.

In an embodiment, the ceramic slurry used in the present invention is colloidal silica. The slurry made from colloidal silica is very stable, chemically inert, has larger pour weight, is resistant to high temperatures & thermal shock and has little shrinkage.

Figure 3C:
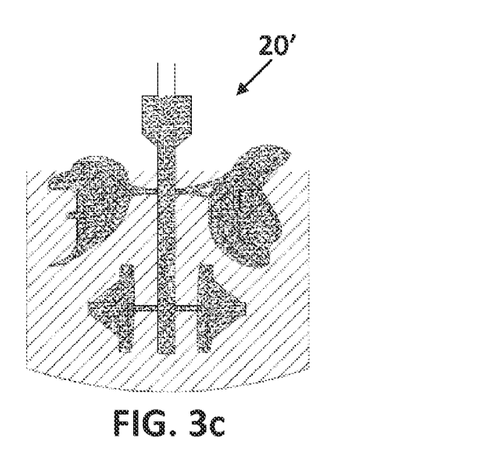
Figure 3D:
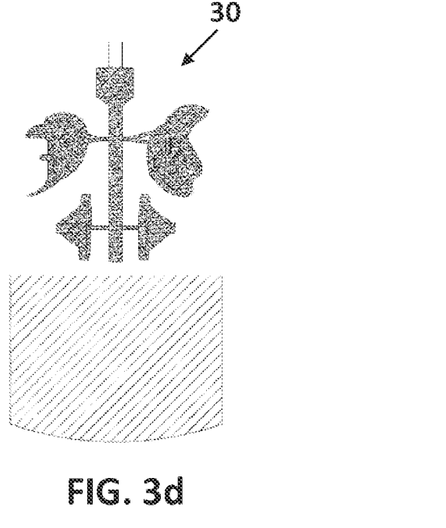

Once the ceramic slurry is formed, the laminated template assembly 20' is dipped in the ceramic slurry as shown in FIGS. 3c and 3d to form the mold 30. The laminated template assembly 20' may be either dipped once or multiple times depending on the desired thickness of the mold 30. In present invention, the template assembly 20 is dipped multiple times to achieve a thickness ranging from 03 mm to 10 mm, more preferably, 05 mm to 08 mm.

In an embodiment, the ceramic slurries used in the present invention have varying mesh sizes. The ceramic slurry used for the first dip may have a mesh size in the range of 250 mesh to 350 mesh followed by decreased mesh sizes in the range of 100 mesh to 200 mesh.

The mold 30 is then subjected to a curing process at step 209 to form a cured mold 30a. The mold 30 is subjected to air dying at a temperature between 22° C. to 24° C. The time for air drying the mold may range from 04 hours to 20 hours more preferably 8 hours to 15 hours.

Figure 3E:
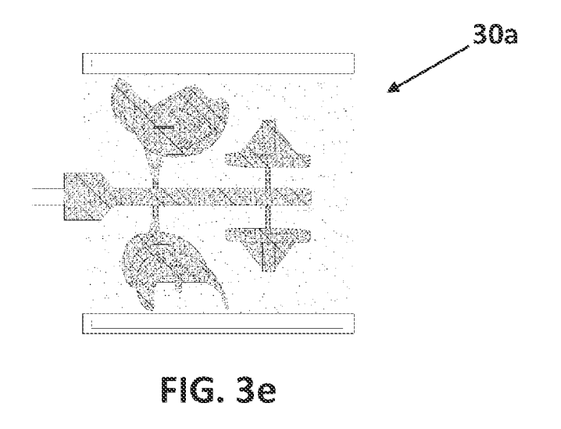

At step 211, the cured mold 30a is subjected to refractory sand rain process as shown in FIG. 3e. For this process, the cured mold 30a may be transferred to a specialized chamber. The process involves spraying or showering of pre-dried sand over the cured mold 30a to form a sand coated mold 30b. The cured mold 30a may be continuously or periodically rotated in a clockwise and/or an anti-clock wise direction to achieve a uniform coating of sand over the cured mold 30a. Further, spraying ensures even deposition of sand over the cured mold 30a.

Figure 3F:
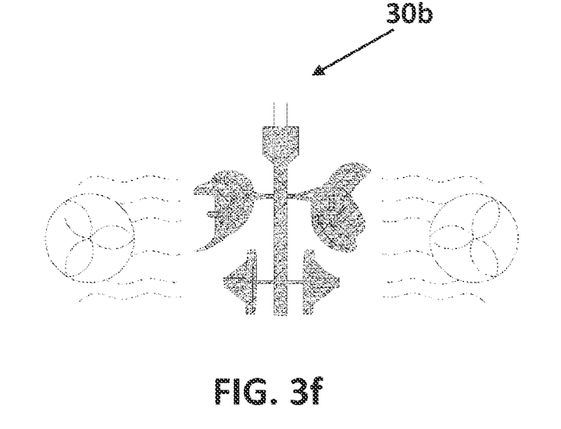

The sand coated mold 30b may be dried in order to remove any residual moisture that may be present over the sand coated mold 30b as shown in FIG. 3f.

At the end of this step, the sand coated mold 30b includes three layers, namely, an outermost layer of sand, a middle layer of ceramic mold and an innermost layer of laminated wax.

At step 213, the sand coated mold 30b is subjected to a de-waxing process in order to remove the innermost layer of the sand coated mold 30b to form a de-waxed mold 30c.

Figure 3G:
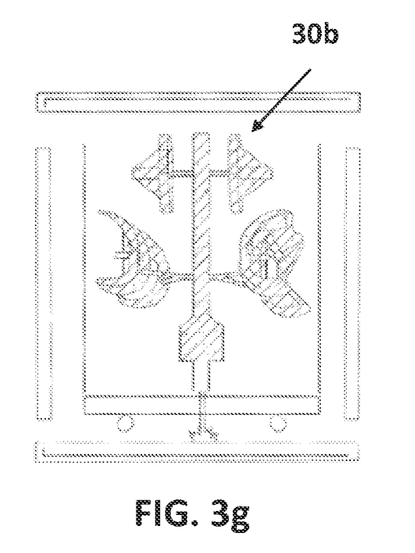

The process involves subjecting the sand coated mold 30b to high temperatures that result in rapid melting of wax and its removal from the sand coated mold 30b. In an embodiment, the process is carried out in a manner in which the sand coated mold 30b is placed in an inverted position while heating, in order to facilitate draining of melted wax from the sand coated mold 30b (as shown in FIG. 3g). in an embodiment, the sand coated mold 30b is placed in an autoclave for few seconds to minutes at a temperature ranging from 80° C. to 200° C. for de-waxing. The molten wax exists from the sand coated mold 30b and may be collected for further use after usual cleaning and filtration.

In an embodiment, autoclaving is continued until all the residual wax is removed from the sand coated mold 30b. Autoclaving the sand coated mold 30b also results in further drying and strengthening the sand coated mold 30b.

After de-waxing process, the de-waxed mold 30c is allowed to dry completely. The de-waxed mold 30c hence achieved has customized shape and dimensions according to the patient's anatomy.

Figure 3H:
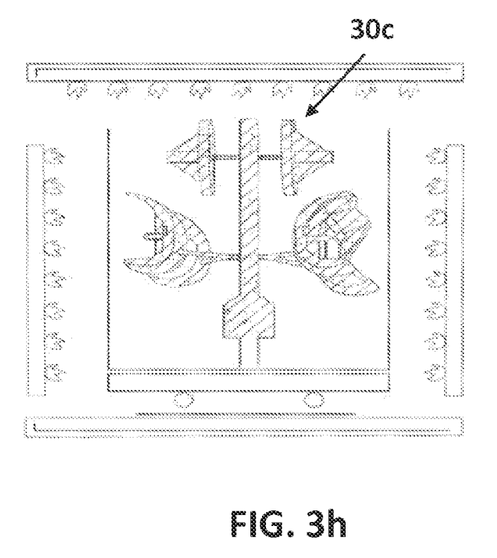

At step 215, the de-waxed mold 30c is baked to form a baked mold 30d as shown in FIG. 3h. Baking may involve pre-heating and conditioning of the de-waxed mold 30c. The process of baking ensures complete removal of the residual wax that might be present after de-waxing. Further, baking process also strengthens the de-waxed mold 30c (ceramic mold) to that it may withstand high temperatures at the time of subsequent steps of the method 200. The laminated layer also gets fully removed/burnout during pre-heating and baking processes which help in achieving smooth inner surface with almost no micro pores and cracks with desired dimensions of the implant 100.

The baking process may be conducted at a temperature ranging between 700° C. to 1200° C. Alternately, the baking temperature may be maintained around 50-100° C. less than the liquid temperature of the metal or its alloy to be poured.

Figure 3I:
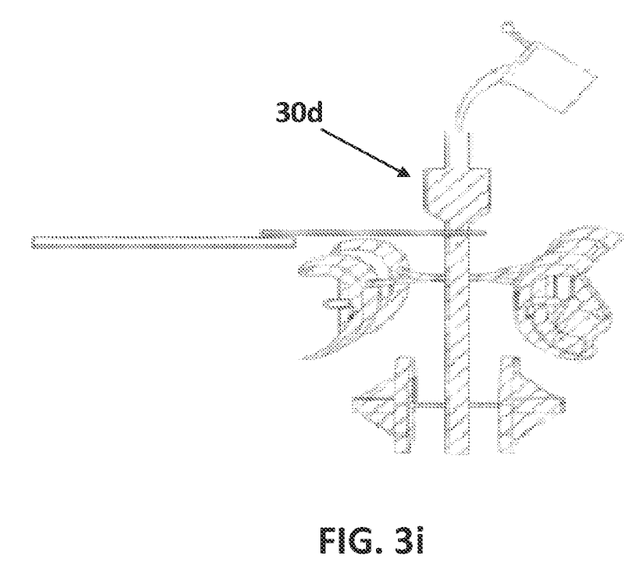

At step 217, the baked mold 30d is subjected to pouring to form a casted mold as shown in FIG. 3i. In an embodiment, a metal alloy is used for pouring. Prior to baking, one or more metal alloys may be melted in an induction furnace at a temperature ranging from 1000° C. and 1500° C. temperature based on the melting point of the metal alloy used.

In a preferred embodiment, the ingots of CoCrMo alloy are procured and subjected to high temperatures for melting. The molten metal alloy is then poured onto the baked mold 30d that has been maintained at a steady temperature. The pouring temperature is an important parameter for casting as it may affect the hardness, surface roughness and dimensional accuracy. The pouring temperature may range between 1200° C. and 1500° C. temperature.

In the present invention, provisions are made to prevent cooling of the molten metal while travelling through the baked mold 30d.

Once the molten metal is poured inside the baked mold 30d, it is then allowed to solidify and take the shape of the baked mold 30d at step 219. In an embodiment, the casted mold is further allowed to cool to form the desired shape of tibial and femoral implants.

Cooling and solidification may be accomplished in two steps. Initially, the casted mold is air cooled for a period of 01 hour to 02 hours. Post air cooling, the casted mold is subjected to water jet cooling in which water jets are sprayed over the casted mold. Water jets cool the casted mold on one hand and on the other, help to crack and subsequently fragment the mold since, ceramic material does not adhere to the casted metal.

Additionally, the residual ceramic in the casted mold may be further removed to form a casted implant 30e. In an embodiment, such step involves soft and gentle hammering with the help of a rubber lined hammer which does not damage the casted metal.

At step 221, the casted implant 30e may be subjected to heat treatment and finishing processes. Heat treatment of the casted implant 30e includes hipping and annealing. Hipping process of the casted implant 30e may be performed at a temperature range lying between 1000° C. and 1100° C. at a pressure in the range between 1000 and 1200 atmosphere. Annealing process may be performed at a pre-defined temperature ranging between 900° C. and 1100° C. and at a pressure less than 2 mm of mercury. In an embodiment, the above pressure and temperature conditions may be maintained for a predefined time i.e. for approximately 10 minutes to 6 hrs, more preferably, from 50 minutes to 5 hrs, and after that the heat treated implant may be allowed to cool to 100° C.

The step of heat treatment improves the microstructure of the implant surface and removes micro pores therein to reduce the brittleness of the casted implant 30e.

Figure 3J:
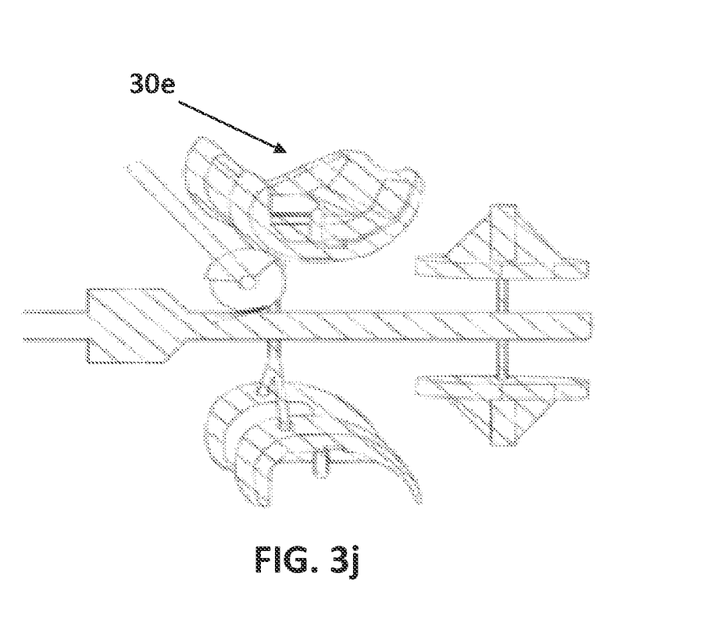

Subsequently, the casted implant 30e is subjected to a finishing process. In an embodiment, the finishing process involves grinding of the casted implant 30e followed by machining and polishing to form the implant 100 as shown in FIG. 3j. The process of finishing may take place in a conventional machine, say, a CNC (Computerized Numerical Control) machine.

The process results in formation of the implant 100 with superior finishing and precise dimensions to conform a patient anatomy. The rejection level of implants manufactured using the present invention was found to be below 10%.

At step 223, the implant 100 undergoes a process of surface treatment. The steps involved in the process of surface treatment may include any conventional set of steps. In an embodiment, the steps of surface treatment as disclosed in the pending patent application no. 201921048709 are applicable in the instant application as well.

Figure 3K:
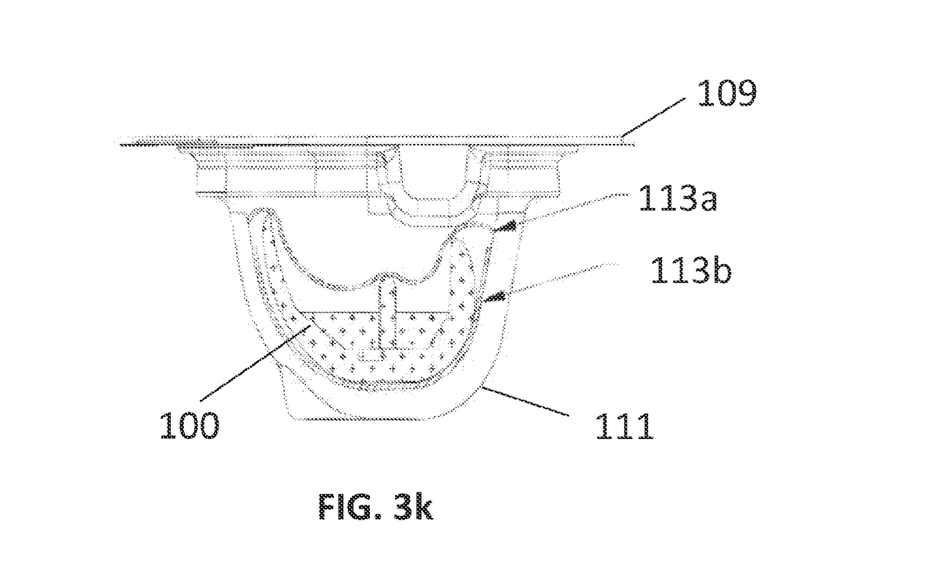

At step 225, the implant 100 is further packed to deliver it to the implantation site without hampering the quality of the implant 100 during storage or transportation. The packaging of the implant 100 is carried out in three enclosures or devices designed to specifically hold the implant 100 during transportation. The said device as depicted in FIG. 3k of the present invention includes an inner femoral tray (not shown), femoral retainer 109 and outer femoral tray 111 which are made from one or more medical grade polymer sheets including polypropylene (PP), polyethylene (PE), polystyrene (PS), acrylonitrile butadiene (ABS), polyvinyl (PV) and polyethylene terephthalate (PET). To ensure protection of the said implant 100 during transportation, the implant 100 is placed or wrapped in a sleeve or sheet made from polyvinyl (PV) (marked as top 113a and bottom 113b sleeves in FIG. 3k) and thus helps to secure the implant 100. To ensure removal of the unwanted debris or particles the said packaging process is carried out in laminar air flow.

Further, the packaged implant 100 may be subjected to a sterilization process. The sterilization can be done using any radiation sterilization technique like e-beam radiation sterilization or gamma sterilization. In an embodiment of the present invention, the packaged implant 100 is sterilized using gamma radiation sterilization.

EXAMPLES

Example 1 (Prior Art)

The knee implant is manufactured using the metal 3-D printing. The implant is manufactured using a technique wherein the cobalt-chromium—molybdenum alloy is melted and the implant is formed layer by layer. The implant when manufactured using the layer by layer deposition method caused formation of small cavities resulting in increased porosity. The increase in porosity caused decrease in implant density which made them more prone to cracks when exposed to high loads thus affecting the mechanical properties of implant that cannot withstand the cyclic stresses at the implantation site. Once 3D printing is completed, the implant is further subjected to a machining process. Even after machining of implant, rejection of around 30% was observed when the implants are manufactured using metal 3-D printing.

Example 2 (Prior Art)

The patient specific knee implant is manufactured using investment casting technique wherein the molds are made up of plaster of paris material. The mold hence formed is further used for casting of a metal implant. However, the plaster of paris mold does not have heat resistant properties and they have high thermal expansion and contraction characteristics. This result in cracks in POP and the POP material stick to the metal when a molten metal at high temperature is poured inside for casting. The cracking of POP structures causes inaccurate dimensions with uneven surface of the implant and hence causing a rejection of around 20%.

Example 3 (Prior Art)

The custom made implant is manufactured using the investment casting technique, The technique involved preparation of a wax template assembly using the EOM 3-D printing process. Further, ceramic material was used for the preparation of the mold due to good thermal resistant property of the ceramic material and its capability of withstanding high temperatures of molten metal during pouring and casting. This helps in achieving uniform and smooth surface with accurate dimensions of implants formed by casting process. The accuracy hence received causes rejection level of around 15%.

Example 4 (Present Invention)

A customize knee implant was fabricated using the present invention with an addition of lamination layer 'LL' over the template assembly. Initially, a customized template assembly 20 was either 3D printed or wax injected in a mold to obtain the desired shape of the implant. The template assembly formed was further brush coated with an adhesive coat 'AC' having a composition of 15 wt % polyamide resin in 85 wt % iso propyl alcohol (IPA). A lamination layer 'LL' was subsequently provided over the adhesive coat 'AC'. A solution of low density polyethylene having a concentration of 1.5 wt %, dissolved in trichloro ethane was applied over the adhesive coat 'AC'. The thickness of the adhesive layer and the lamination layer 'LL' was observed to be around 5 μm and around 30 μm respectively.

The lamination layer 'LL' was further subjected to around 5 to 7 stages of dip coating of ceramic thick slurry. The dry ceramic coated template assembly 20 was further showered with sand rain to prepare the mold and followed by de-waxing & baking process. Subsequent to the above processes, the finished casted parts were subjected to heat treatment process.

The above disclosed method reduced the average time of fabrication of the implant by 20% to 25% mainly at the time of buffing, machining and polishing as compared to conventional processes. The hipping time was found to reduce by around 30%. The implant formed by the above process resulted in superior finishing and dimensional accuracy. The overall rejection of the implants was found to be below 10%.

Example 5 (Present Invention)

A standard size implant was manufactured by precious casting technique of the present invention. Initially, a standard or normal size template assembly 20 was either 3D printed or wax injected in a mold to get the desired shape of the implant. The template assembly formed was further coated with an adhesive coat 'AC' having a composition of 15 wt % of hydrocarbon resin dissolved in trichloro ethane. A lamination layer 'LL' was subsequently provided over the adhesive coat 'AC'. The lamination layer 'LL' included a composition of 15 wt % LDPE dissolved in trichloro ethane. The thickness of the adhesive layer and the lamination layer 'LL' was observed to be around 4 μm and around 40 μm respectively.

The lamination layer 'LL' was further subjected to around 5 to 7 stages of dip coating of ceramic thick slurry. The dry ceramic coated template assembly 20 was further showered with sand rain to prepare the mold and followed by de-waxing & baking process. Subsequent to the above processes, the finished casted parts were subjected to heat treatment process.

The above disclosed method reduced the average time of fabrication of the implant by 20% to 25% mainly at the time of buffing, machining and polishing as compared to conventional processes. The hipping time was found to be reduced by around 30%. The implant formed by the above process resulted in superior finishing and dimensional accuracy. The overall rejection of the implants was found to be below 10%.

The above examples clearly establish that the implants 100 fabricated using the method of the present invention reduce the rejection rate to less than 10%. Thus, a rejection rate of less than 10% amounts to saving thousands of kilograms of metal that are wasted when using conventional implants.

Hence, the present invention addresses the limitations of the conventional methods used for fabrication of implants to yield an efficient as well as competitive method.

The scope of the invention is only limited by the appended patent claims, More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

We claw:

1. A method of manufacturing an implant (100), the method comprising:
   a. preparing a template assembly (20), the template assembly (20) being made from wax;
   b. providing a lamination layer over the outer surface of the template assembly (20) resulting in a laminated template assembly (20'), the lamination layer 'LL' being composed of at least one polymer dissolved in one or more solvents;
   c. preparing a mold (30) by providing one or more coating layers of a pre-defined coating material over the laminated template assembly;
   d. providing pre-dried sand over the mold (30) to form a sand coated mold (30b);
   e. de-waxing and baking the sand coated mold (30b) for melting out the template assembly (20) to form a de-waxed mold (30c);
   f. pouring a pre-defined casting material over the de-waxed mold (30c) to form a casted mold;
   g. cooling and solidifying the casted mold to form a casted implant (30e); and
   h. heat treating and finishing the casted implant (30e) to form an implant (100).

2. The method of manufacturing an implant as claimed in claim 1 wherein, the preparing the template assembly (20) includes fabricating a template assembly (20) using fused deposition modelling.

3. The method of manufacturing an implant as claimed in claim 1 wherein, the preparing the template assembly (20) includes preparing a customized template assembly (20) using one or more anatomical characteristics derived from simulation of a radiological imaging technique.

4. The method of manufacturing an implant as clamed in claim 3 wherein the one or more anatomical characteristics include one or more of thickness, curvature and/or size of an implantation site.

5. The method of manufacturing an implant as clamed in claim 1 wherein the wax may include one or more of paraffin wax, bees wax, montan wax, carnabua wax or a blend of wax.

6. The method of manufacturing an implant as clamed in claim 1 wherein providing the lamination layer 'LL' includes first providing an adhesive coat 'AC' over the template assembly (20).

7. The method of manufacturing an implant as clamed in claim 6 wherein the adhesive coat 'AC' is composed of one or more resins dissolved in one or more solvents.

8. The method of manufacturing an implant as clamed in claim 6 wherein the adhesive coat 'AC' includes a thickness ranging between 2 µm and 6 µm.

9. The method of manufacturing an implant as clamed in claim 1 wherein the lamination layer 'LL' includes a composition having LDPE in a concentration of 5 wt %-40 wt % dissolved in 50 –90 wt % of solvents.

10. The method of manufacturing an implant as clamed in claim 1 wherein the lamination layer 'LL' includes a thickness ranging between 10 µm and 80 µm.

11. The method of manufacturing an implant as clamed in claim 1 wherein the preparing the mold (30) includes providing one or more coating layers having a thickness ranging between 03 mm to 10 mm.

12. The method of manufacturing an implant as clamed in claim 1 wherein the pre-defined coating material includes ceramic slurry.

13. The method of manufacturing an implant as clamed in claim 1 wherein the de-waxing involves autoclaving the sand coated mold (30*b*) at a temperature ranging from 80° C. to 200° C.

14. The method of manufacturing an implant as clamed in claim 1 wherein the baking involves a temperature ranging between 700° C. to 1200° C.

15. The method of manufacturing an implant as clamed in claim 1 wherein the pre-defined pouring material is molten cobalt chromium molybdenum alloy.

16. The method of manufacturing an implant as clamed in claim 1 wherein the cooling and solidifying includes air cooling the casted mold for 1-2 hours followed by water jet cooling of the casted mold.

17. The method of manufacturing an implant as clamed in claim 1 wherein the heat treating and finishing includes hipping and annealing of the casted implant (30*e*).

18. The method of manufacturing an implant as clamed in claim 1 wherein the heat treating and finishing is followed by surface treating the implant (100).

\* \* \* \* \*